(12) United States Patent
Kimmel

(10) Patent No.: US 10,542,929 B2
(45) Date of Patent: Jan. 28, 2020

(54) DETERMINING CONDITIONS BASED ON INTRAORAL SENSING

(71) Applicant: Dustin Ryan Kimmel, San Francisco, CA (US)

(72) Inventor: Dustin Ryan Kimmel, San Francisco, CA (US)

( * ) Notice: Subject to any disclaimer, the term of this patent is extended or adjusted under 35 U.S.C. 154(b) by 183 days.

(21) Appl. No.: 15/439,968

(22) Filed: Feb. 23, 2017

(65) Prior Publication Data

US 2017/0238863 A1 Aug. 24, 2017

Related U.S. Application Data

(60) Provisional application No. 62/298,930, filed on Feb. 23, 2016.

(51) Int. Cl.
*A61B 5/00* (2006.01)
*A61B 5/16* (2006.01)
*A61B 5/05* (2006.01)
*A61B 5/107* (2006.01)

(52) U.S. Cl.
CPC .......... *A61B 5/4552* (2013.01); *A61B 5/0088* (2013.01); *A61B 5/05* (2013.01); *A61B 5/1077* (2013.01); *A61B 5/165* (2013.01); *A61B 5/4803* (2013.01); *A61B 5/486* (2013.01); *A61B 5/682* (2013.01); *A61B 5/7267* (2013.01); *A61B 5/7282* (2013.01); *A61B 5/7455* (2013.01)

(58) Field of Classification Search
CPC .................................................. A61B 5/4552
USPC ......................................................... 710/73
See application file for complete search history.

(56) References Cited

U.S. PATENT DOCUMENTS

| | | | | |
|---|---|---|---|---|
| 4,310,002 A * | 1/1982 | Takinishi | ............ | A61B 5/0534 434/185 |
| 5,212,476 A * | 5/1993 | Maloney | ............ | A61B 5/04886 340/4.11 |
| H001497 H * | 10/1995 | Marshall | ........................ | 704/254 |
| 5,460,186 A * | 10/1995 | Buchhold | ................. | A61F 4/00 340/4.11 |
| 5,523,745 A * | 6/1996 | Fortune | ..................... | A61F 4/00 340/4.12 |
| 5,579,284 A * | 11/1996 | May | ........................ | H04B 11/00 340/850 |
| 5,603,065 A * | 2/1997 | Baneth | ..................... | A61F 4/00 340/4.14 |
| 5,631,669 A * | 5/1997 | Stobbs | ................. | G06F 3/03543 345/156 |
| 5,792,067 A * | 8/1998 | Karell | .................. | A61N 1/0548 128/848 |

(Continued)

OTHER PUBLICATIONS

James Robert Brasic, "Tardive Dyskinesia", Feb. 9, 2012, Medscape Reference: Drugs, Diseases, and Procedures, p. 1. (Year: 2012).*

*Primary Examiner* — Jason C Olson

(57) ABSTRACT

Techniques, methods, systems, devices, and computer readable medium are disclosed from an oral cavity of a user identifying a feature in the user's oral cavity, tracking the feature as it changes, and determining a condition based on the tracking of the feature in the user's oral cavity. The user can use an interface provided by the device's user interface for activities such as biofeedback, controlling functions of the device and other devices, receiving information from external devices or the device, etc.

13 Claims, 11 Drawing Sheets

(56) References Cited

U.S. PATENT DOCUMENTS

| | | | | |
|---|---|---|---|---|
| 5,828,758 | A * | 10/1998 | Byce | G09B 21/00 381/70 |
| 6,006,175 | A * | 12/1999 | Holzrichter | A61B 5/0507 704/205 |
| 6,222,524 | B1 * | 4/2001 | Salem | A61F 4/00 340/4.11 |
| 6,231,500 | B1 * | 5/2001 | Kehoe | A61F 5/58 600/23 |
| 6,402,707 | B1 * | 6/2002 | Ernst | A61B 5/1076 600/590 |
| 6,938,576 | B2 * | 9/2005 | van der Lely | A01K 1/12 119/14.02 |
| 7,071,844 | B1 * | 7/2006 | Moise | G06F 3/011 340/4.11 |
| 8,924,214 | B2 | 12/2014 | Willey | |
| 2002/0143276 | A1 * | 10/2002 | Ernst | A61C 19/00 600/590 |
| 2003/0120183 | A1 * | 6/2003 | Simmons | A61F 4/00 600/595 |
| 2005/0070782 | A1 * | 3/2005 | Brodkin | A61C 13/0004 600/407 |
| 2007/0106138 | A1 * | 5/2007 | Beiski | A61B 5/682 600/349 |
| 2009/0271936 | A1 * | 11/2009 | Walanski | A61B 5/0088 15/105 |
| 2009/0309747 | A1 * | 12/2009 | Ghovanloo | A61F 4/00 340/686.1 |
| 2011/0159453 | A1 * | 6/2011 | Kotlarchik | A61B 5/0088 433/27 |
| 2012/0240934 | A1 * | 9/2012 | Holzrichter | A61B 5/0826 128/204.23 |
| 2012/0259554 | A1 * | 10/2012 | Chen | A61F 4/00 702/19 |
| 2012/0295216 | A1 * | 11/2012 | Dykes | A61C 17/22 433/27 |
| 2012/0329406 | A1 * | 12/2012 | Christensen | H01Q 1/44 455/90.1 |
| 2015/0140502 | A1 * | 5/2015 | Brawn | A61C 7/08 433/24 |
| 2015/0208979 | A1 * | 7/2015 | Cunningham | A61B 5/4552 600/590 |
| 2015/0301619 | A1 * | 10/2015 | Menon | A61F 4/00 345/156 |
| 2016/0027441 | A1 * | 1/2016 | Liu | G10L 15/25 704/255 |
| 2016/0113495 | A1 * | 4/2016 | Nanjundappa | A61C 1/0046 433/29 |
| 2017/0143259 | A1 * | 5/2017 | Kent | A61B 5/4836 |
| 2017/0311872 | A1 * | 11/2017 | Matsuda | A61B 5/00 |
| 2018/0116548 | A1 * | 5/2018 | Morgan | A61B 5/062 |

* cited by examiner

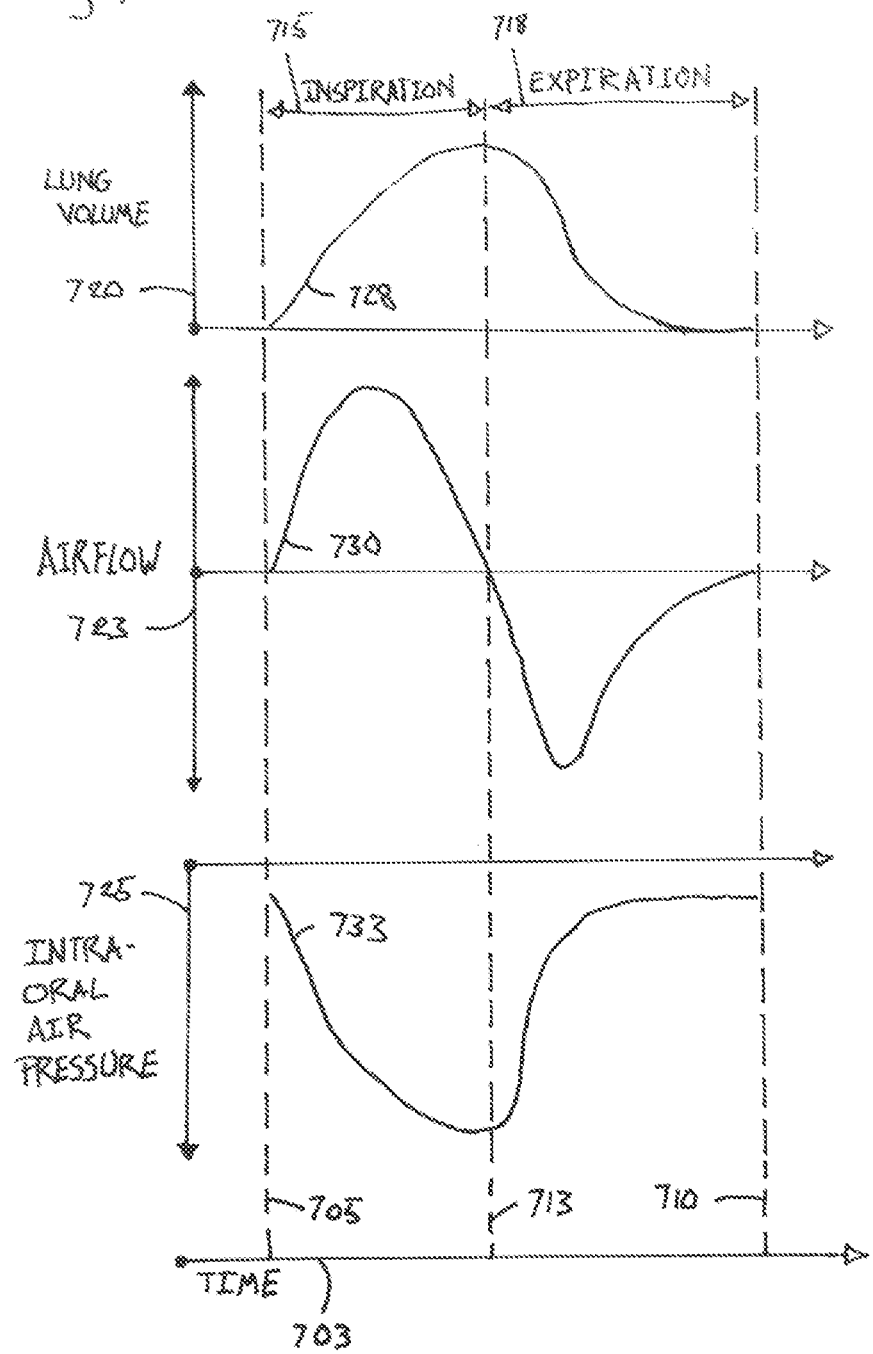

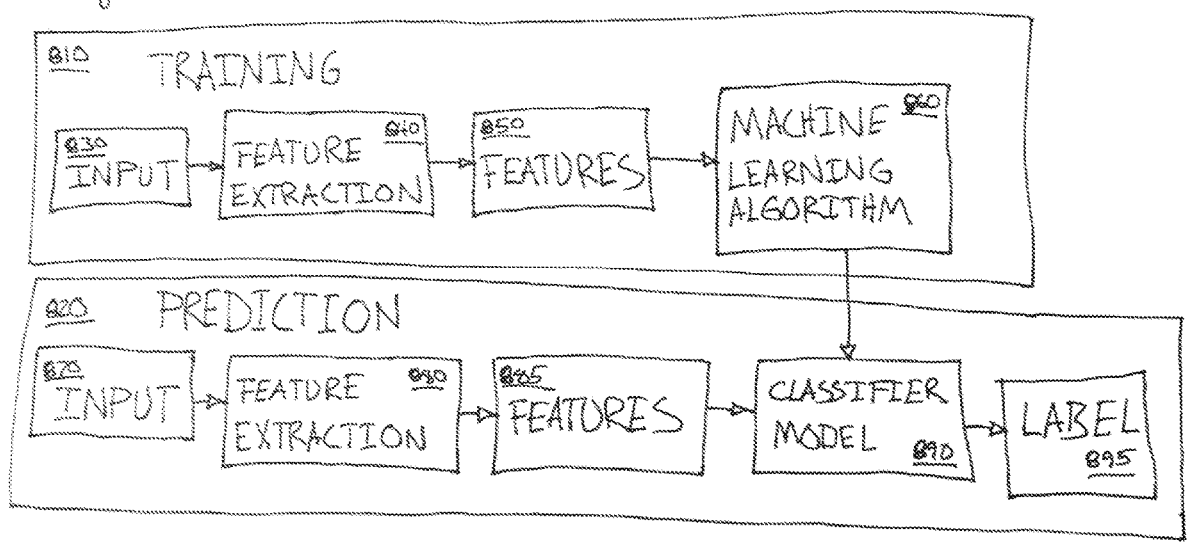

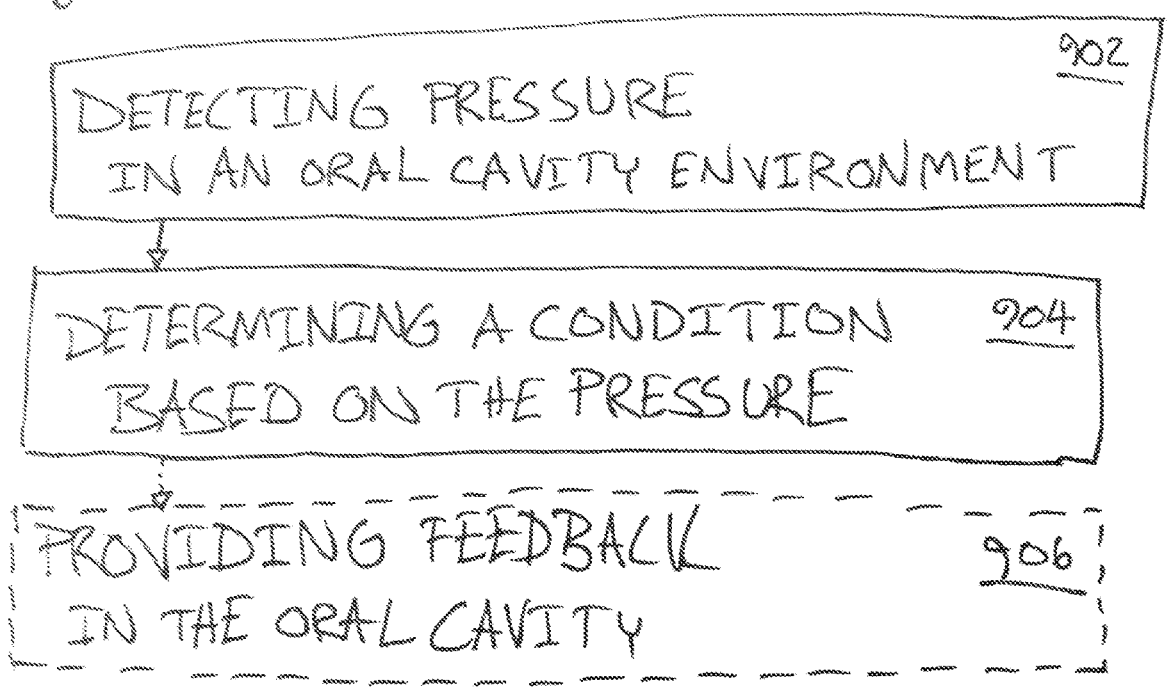

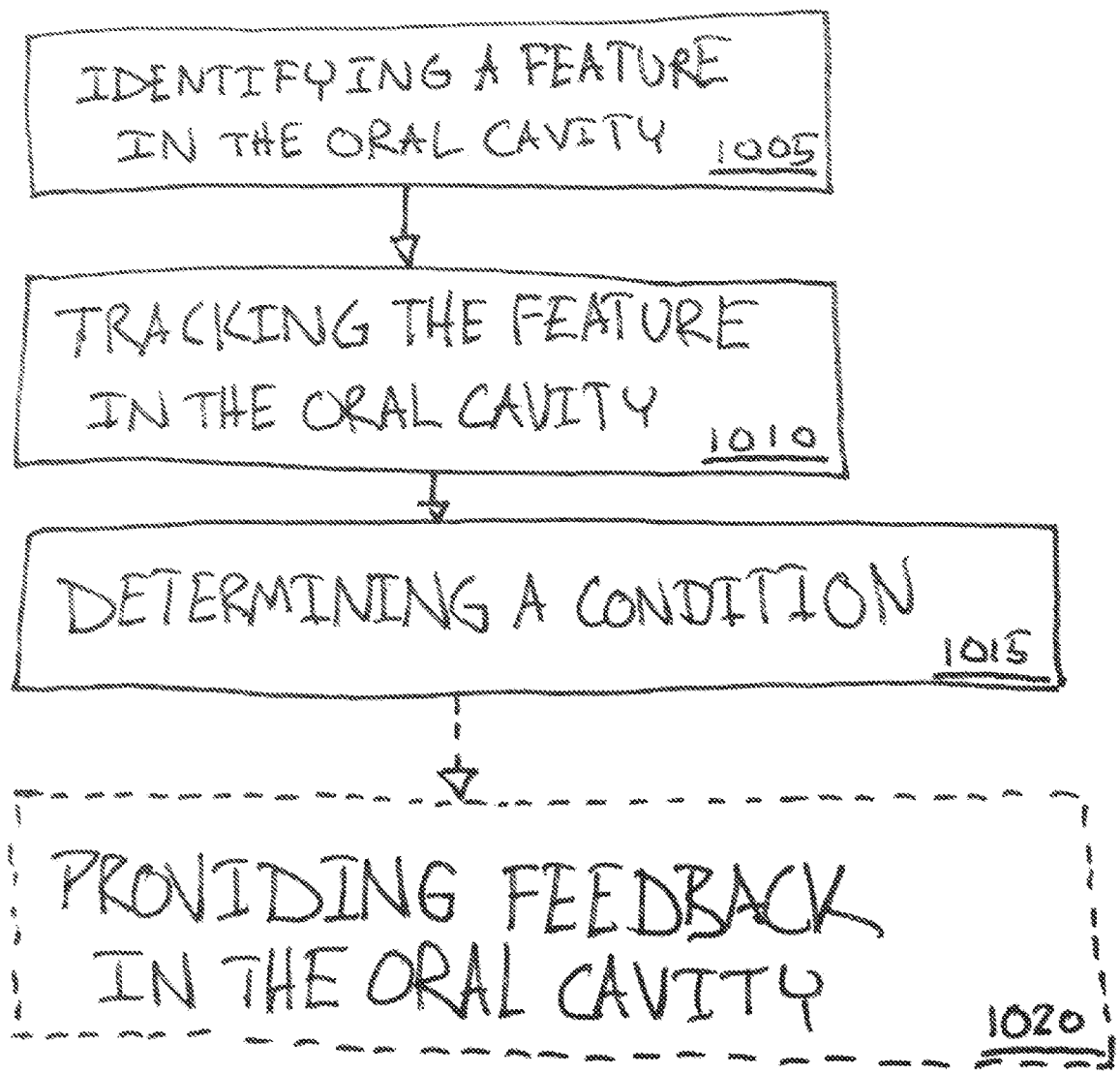

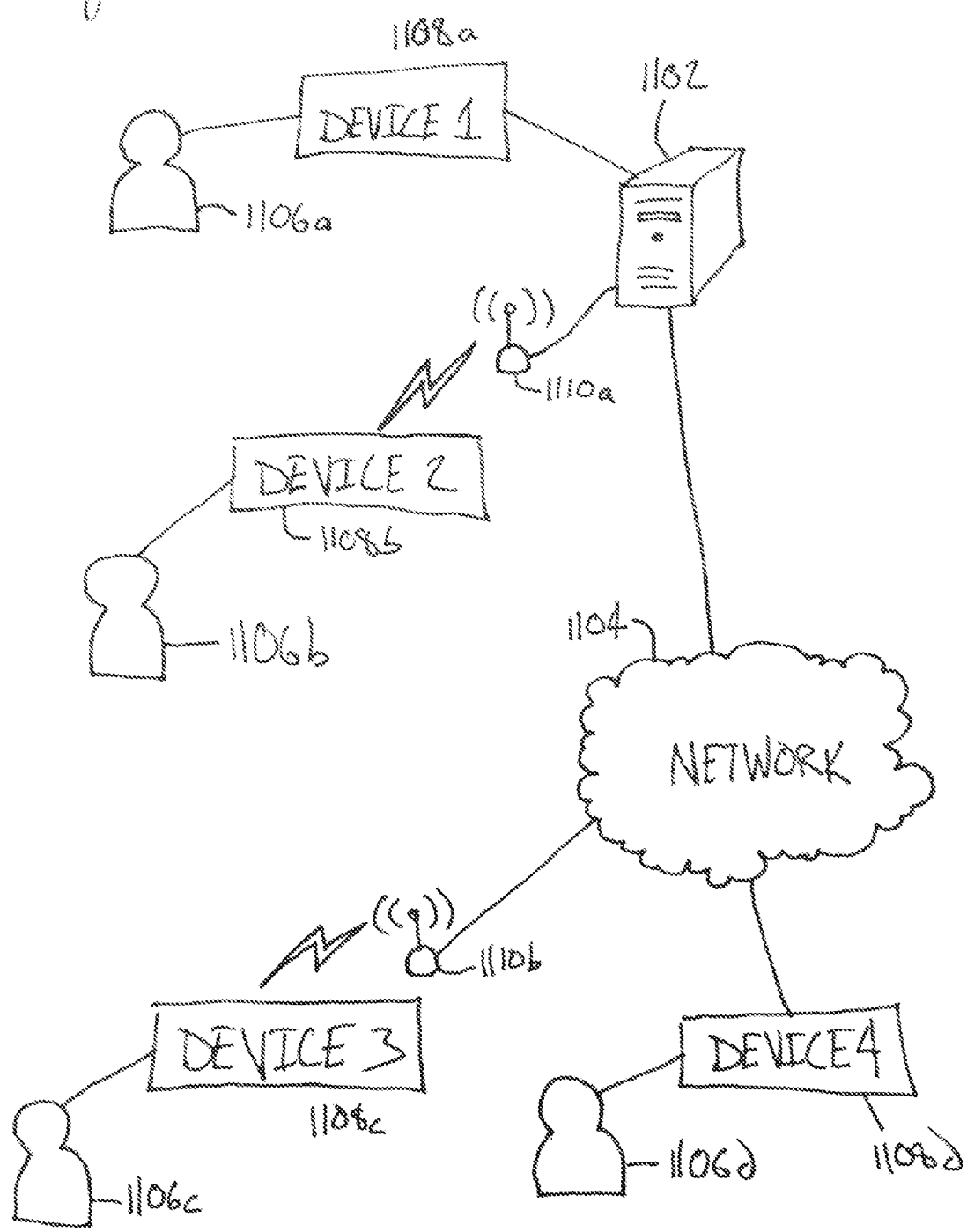

DETERMINING CONDITIONS BASED ON INTRAORAL SENSING

CROSS-REFERENCE

This application claims benefit and priority of U.S. Provisional Application No. 62/298,930, filed Feb. 23, 2016, entitled, "INTRAORAL SENSING, INTERPRETATION AND APPLICATION." The entire content of the 62/298,930 application is incorporated herein by reference for all purposes.

BRIEF DESCRIPTION OF THE DRAWINGS

FIG. 7 is an example graph of multiple respiration aspects over time;

FIG. 8 is a block diagram is an example of one machine learning process, supervised classification, that can be implemented in some embodiments of the invention;

FIG. 9 is a flow diagram of an example embodiment for determining a condition using pressure;

FIG. 10 is a flow diagram of an example embodiment for determining a condition based on tracking a feature in the oral cavity; and FIG. 11 is an example system figure for a simplified crowdsourcing system, wherein the server receives data from a plurality of device.

DETAILED DESCRIPTION

Figure 1:
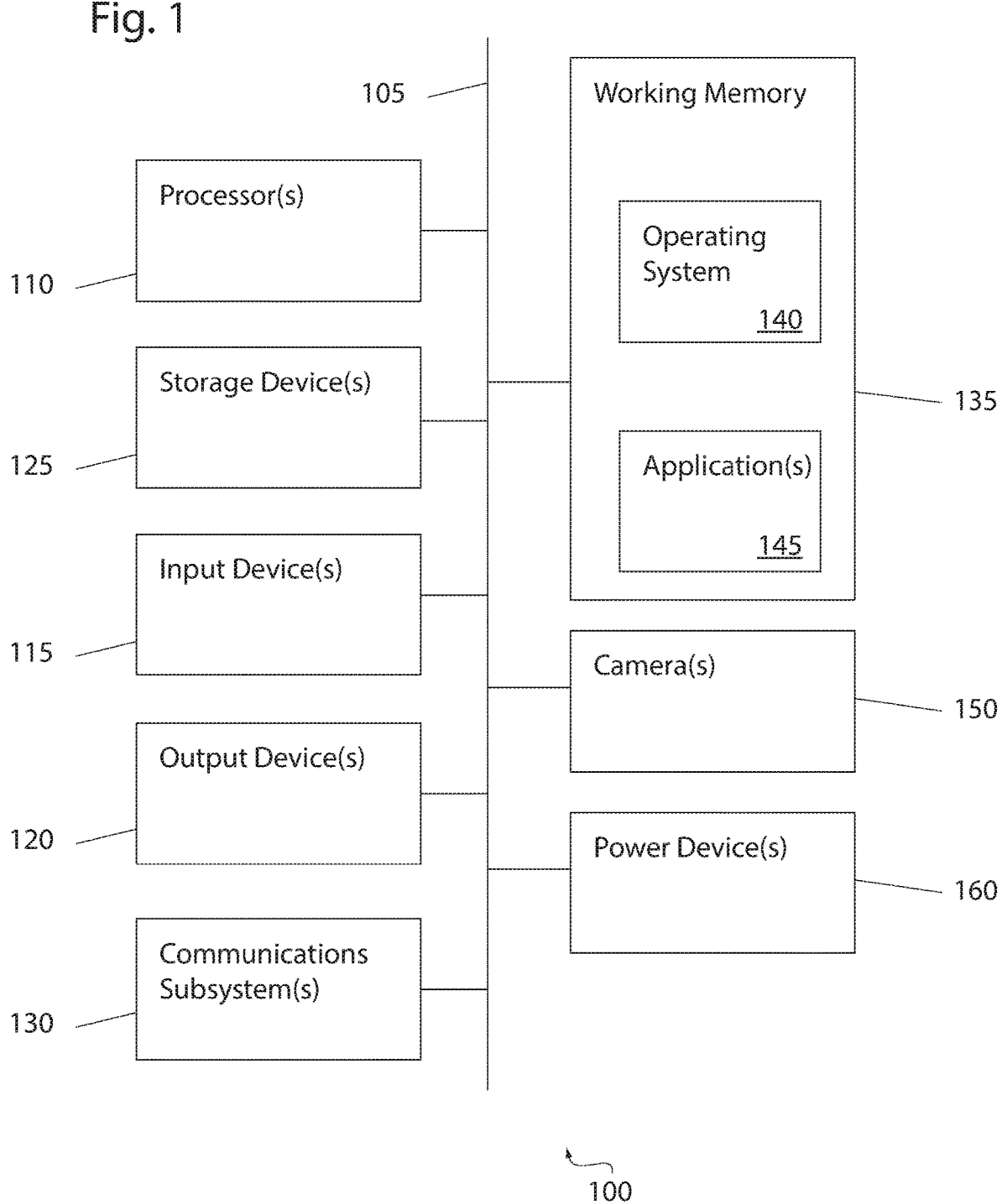
FIG. 1 illustrates an example device incorporating parts of the device employed in practicing embodiments of the invention.

Aspects of this disclosure discuss novel techniques for sensing activity within an oral cavity and capture information associated with the movement of animal parts and foreign objects within the oral cavity. Such techniques enable detection/observation of movement of the animal parts and/or foreign objects with several degrees of freedom (e.g., 5 DOF, 6 DOF) and provide a variety of functions (e.g., detection of commands) as disclosed in further detail below. In at least one embodiment, a variety of sensors may be used for detecting/observing movement of the animal parts or foreign objects in the oral cavity.

The present invention provides a new way of first sensing and interpreting data observed from the mouth, and then creating commands or information based on those and/or other data and/or observations. This invention employs an intraoral device, a device placed wholly, or partially in the mouth of a subject, and capable of detecting inputs involving movement, material, and/or pressure. Based on inputs, the device can identify features in the oral cavity, such as states of the physical shape of the oral cavity and/or its tissues and/or its contents, and/or the air pressure within the oral cavity. The device can track a change in a feature, such as a movement and/or a pressure change, and then cause itself to perform an operation associated with the change.

The device, comprised of a computer system comprised of one or more sensors, is placed in the mouth of a user. The system is protected and arranged in an enclosure in such a way that each sensor has access to the oral cavity with respect to its intended sensing purpose. For instance, a gas pressure sensor would be embedded in the enclosure so as to allow access to the gas in the oral cavity. Likewise, a radar transmitter and receiver would be embedded in the enclosure in an orientation with a vantage to observe the parts of the oral cavity that can change shape and/or move, namely the tongue, lower jaw, lips, cheeks, and pharynx.

The device's enclosure houses and protects the system from damage, such as exposure of electronics to the moisture of the mouth environment, and can have affordances that can be used for anchoring, affixing, or otherwise stabilizing the device in relationship to the mouth environment, such as a mouthguard shape that stays put in the maxilla of a user. By helping to stabilize the device, these affordances can also help to stabilize sensor frame of reference and decrease bad readings caused by unwanted movement of the device in relationship to the mouth environment.

An advantage to the present invention is that, because humans have a capacity for language that involves intricate control and manipulation of the oral cavity environment, by observing changes in the oral cavity and performing associated operations, the invention can act as a tool to harnesses that natural human capacity and employ it in new ways.

Another advantage to the present invention is that the inputs to the device can be everyday activities, like breathing and/or motions of the tongue, lips, jaw, cheeks.

Yet another advantage to the present invention is that the inputs to the device can be activities that don't require direct tissue contact with the device, such as breathing, and/or movement of the tongue in the oral cavity, unlike, for example, a tongue joystick, which requires direct manipulation of the input.

And one more advantage to the present invention is that some inputs, like the physical state of the oral cavity, have almost unlimited degrees of freedom, in that a mouth, comprising a tongue, can change in myriad, independent ways, and therefore the device can determine many more conditions at once than alternative devices, like a foot pedal, for instance, which only has one degree of freedom.

FIG. 1 illustrates an example device incorporating parts of the device employed in practicing embodiments of the invention. An example device as illustrated in FIG. 1 may be incorporated as part of the described computerized device below. For example, device 100 can represent some of the components of a mobile device. A mobile device may be any computing device with an input sensory unit, like a touchpad, and an output unit, like a speaker. Examples of a mobile device include, but are not limited to, video game consoles, tablets, smart phones, camera devices and any other portable devices suitable for performing embodiments of the invention. FIG. 1 provides a schematic illustration of one embodiment of a device 100 that can perform the methods provided by various other embodiments, as described herein. FIG. 1 is meant only to provide a generalized illustration of various components, any or all of which may be utilized as appropriate. FIG. 1, therefore, broadly illustrates how individual system elements may be implemented in a relatively separated or relatively more integrated manner. FIG. 1 is an example portable processing device or mobile device that may use components as described in reference to FIG. 1. In some embodiments, only some of the components described in FIG. 1 are implemented and enabled to perform embodiments of the invention. For example, a touchpad device may have one or more touchpads, storage, or processing components along with other components described in FIG. 1.

The device 100 is shown comprising hardware elements that can be electrically coupled via a bus 105 (or may otherwise be in communication, as appropriate). The hardware elements may include, but are not limited to, one or more power devices 160, including without limitation one or more power storage and/or distribution devices (such as a battery) and/or one or more power generation, storage, and distribution devices (such as a combination of power generator, power management device, and a battery). In other embodiments, power and/or data might be distributed via one or more separate buses, or a combination of buses, and/or individual components of device 100 might have independent or external power device(s) 160. The hardware elements may include, but are not limited to, one or more processors 110, including without limitation one or more general-purpose processors and/or one or more special-purpose processors (such as digital signal processing chips, graphics acceleration processors, random number generator and logic for cryptography, and/or the like). The hardware elements may also include one or more signal-creating input devices 115 which can sense analog input in the area of the mouth environment. One or more input devices 115 can include without limitation a touchpad, sensors, sensor devices (example sensor devices discussed in figures and later paragraphs), a microphone, a pushbutton, a gyroscope, and/or an accelerometer and/or the like. For example, a microphone might sense the analog input of sound projected into the mouth environment. The hardware elements may also include one or more output devices 120, which can produce a stimulus to a subject and/or mouth environment and can include without limitation a vibration device, a light device, an electric-shock and/or electrode-array device, devices (example devices discussed in figures and later paragraphs), and/or the like. For example, an electrode-array device might produce a stimulus of an electric shock to a person in the oral environment that it might be touching. In addition, hardware elements may also include without limitation one or more cameras 150, as shown in FIG. 1, for acquiring image content in and/or from within the mouth environment.

In other embodiments one or more input devices 115 can include, without limitation: a radar system, that can be comprised of one or more of a transmitter, waveguide, antenna duplexer, and/or receiver, that which can be used to observe and report on the nature of materials and the movement of body parts, tissues, fluids, and/or materials in and/or around the oral cavity; a movement tracking sensor device such as an LED/photodiode tracking device (as found in an optical mouse) and/or more advanced visual-tracking devices, which can be used to observe and report movement information; pressure sensor devices (like a microphone device, piezoelectric devices, and/or an air pressure sensor device), which can be used to observe and report pressure change information such as sound, vocalizations, breathing or physical stress changes; temperature sensor devices (like a thermometer device), which can be used to observe and report body heat, respiration temperature, external temperature, general temperature, or other temperature information; touch sensor devices (like button devices, switch devices, slider devices, bite pressure devices, piezoelectric devices optical touch devices, rotation sensor devices, optical movement tracking devices and touchpad devices), which can be used to observe and report direct physical interaction and movement information and even indirect physical interaction and movement information; air sensor devices (like machine olfaction devices, gas flow monitor devices, and/or chemical identification devices), which can be used to observe and report breathing, temperature, humidity, pressure, gas flow, gas state, and air quality information; material sensor devices (like machine taste devices, chemical sensor devices, salinity sensor devices, blood analysis devices and/or pH sensor devices), which can be used to observe and report chemical makeup information or other physical characteristics of breath, food, saliva, bodily fluids and/or organs; light sensor devices (like photodiode devices, infrared light sensor devices, light meter devices and/or camera devices), which can be used to observe and report light, distance, thickness, color and movement information; acceleration sensor devices (like an accelerometer or a pedometer device) which can be used to observe and report velocity and/or acceleration change and movement force information; and orientation sensor devices (like a compass device, or a digital gyroscope device), which can be used to observe and report orientation and movement information.

In other embodiments one or more stimulus and/or output devices 120 can include, without limitation: electrical stimulator devices (like electrode devices, electrode-array devices, and/or shock devices), which can be used to communicate to or stimulate the user and/or others by applying electric current via electrodes to the surrounding environment (such as to the surface of the tongue, to the interior of the mouth, or to and/or into the tissue of an embedding site); light devices (like indicator light devices, infrared light devices, or laser light or laser pointer devices), which can be used to communicate to the user or others and/or illuminate by creating visible, infrared and/or ultraviolet light and/or light beams (and projected beams can be used as pointing devices or projector displays by the user); tactile, actuator, or touch-based vibration devices (like vibration motor devices, and Braille terminal devices), which can be used to communicate to the user or others by creating vibration based feedback and tactile or touchable states; physical release devices (like metered chemical release devices (which could release chemicals), spray devices, dispenser devices, or pill dispenser devices), which can be used to release matter to communicate to and/or or stimulate the user and others by releasing or dispensing matter into the surrounding environment; and mechanical wave generator devices (like speaker devices and/or vibration devices and/or bone-conduction transducer devices), which can be used to communicate to the user and others by creating sound and other mechanical waves.

In other embodiments one or more power devices 160 could reside apart from the rest of device 100, including, without limitation, outside any primary enclosure, in a separate enclosure, and/or connected by a tether and/or power transfer device. In other embodiments power may be generated by one or more power devices 160 from, including, without limitation, interaction with the chemicals in the internal and/or external environment (such as electrical interaction as in a battery, by using an exposed anode and cathode), and/or interaction with the chemicals and/or pressure of the bloodstream of the user, and/or interaction with the external environment and/or functioning of organisms and/or one or more devices hosted within the device (such as with a genetically-engineered biofuel device and/or biofuel organism that generates power from oxygen and glucose in the bloodstream of a wearer), and/or interaction with temperature differences in the external environment (such as by coupling a generator with a Stirling engine or other heat engine), and/or by movement (such as by coupling a generator with a self-winding mechanism of the type as used in a self-winding watch and/or capturing the energy of actions performed on device 100), and/or by wireless energy transfer (such as by direct induction, resonant magnetic induction or electromagnetic power reception devices (such as RFID tags)).

The device 100 may further include without limitation (and/or be in communication with) one or more non-transitory storage devices 125, which can comprise, without limitation, local and/or network accessible storage, and/or can include, without limitation, a hard drive, a drive array, an optical storage device, a solid-state storage device such as a random access memory ("RAM") and/or a read-only memory ("ROM"), which can be programmable, flash-updateable and/or the like. Such storage devices may be configured to implement any appropriate data storage, including, without limitation, various file systems, database structures, and/or the like.

The device 100 might also include without limitation one or more communications subsystems 130, which can include without limitation a network communications device (wireless and/or wired), an infrared communication device, an optical communications device, a wireless communication device and/or chipset (such as a Bluetooth® device, an RFID device (active, passive, or battery-assisted passive), an 802.11 device, a WiFi device, a WiMax device, cellular communication facilities), any kind of signaling circuitry or communications device, including any kind of EMF transmitter/receiver device (which may, without limitation, transmit, receive, both transmit and receive, reflect and/or alter an outside transmission, and the like) a wireless communications device, and/or the like. Bluetooth is a proprietary open wireless technology standard for wirelessly exchanging data, and RFID, Radio-frequency identification, is a wireless non-contact technology that uses radio-frequency electromagnetic fields to transfer data. Communications subsystem 130 could include, without limitation, one or more antenna devices to broadcast and receive electromagnetic signals. Communications subsystem 130 may permit data to be exchanged with an external and/or remote device (such as a mobile device) and/or network, other devices, and/or any other devices described herein. As described herein, the term "external device" and "remote device" may be used interchangeably, without limiting the scope of the disclosure. For example, the external device discussed above may be the same device as the remote device 930 discussed in FIG. 9.

In many embodiments, the device 100 will further comprise a non-transitory working memory 135, which can include a RAM or ROM device, as described above.

Other devices that communications subsystem 130 may permit data to be exchanged with include without limitation other and/or similar embodiments of the invention in and/or on and/or throughout the body of the wearer, and/or in and/or on and/or the body or bodies of one or more other wearers of such devices.

The device 100 also can comprise software elements, shown as being currently located within the working memory 135, including an operating system 140, device drivers, executable libraries, and/or other code, such as one or more programs or application(s) 145, which may comprise computer programs provided by various embodiments, and/or may be designed to implement methods, and/or configure systems, provided by other embodiments, as described herein. Merely by way of example, one or more procedures described with respect to the method(s) discussed above might be implemented as code and/or instructions executable by a computer (and/or a processor within a computer); in an aspect, then, such code and/or instructions can be used to configure and/or adapt a general purpose computer (or other device) to perform one or more operations in accordance with the described methods.

A set of these instructions and/or code might be stored on a computer-readable storage medium, such as the storage device(s) 125 described above. In some cases, the storage medium might be incorporated within a device, such as device 100. In other embodiments, the storage medium might be separate from a device (e.g., a removable medium, such as a compact disc), and/or provided in an installation package, such that the storage medium can be used to program, configure and/or adapt a general purpose computer with the instructions/code stored thereon. These instructions might take the form of executable code, which can be executable by the device 100 and/or might take the form of source and/or installable code, which, upon compilation and/or installation on the device 100 (e.g., using any of a variety of generally available compilers, installation programs, compression/decompression utilities, etc.), then takes the form of executable code.

Substantial variations may be made in accordance with specific requirements. For example, customized hardware might also be used, and/or particular elements might be implemented in hardware, software (including portable software, such as applets, etc.), or both. Further, connection to other computing devices such as network input/output devices may be employed, for instance, to process sensor data about the mouth environment externally, and/or externally processing data in combination with more data about different mouth environments.

Some embodiments may employ a device (such as the device 100) to perform methods in accordance with the disclosure. For example, some or all of the procedures of the described methods may be performed by the device 100 in response to processor 110 executing one or more sequences of one or more instructions (which might be incorporated into the operating system 140 and/or other code, such as an application 145) contained in the working memory 135. Such instructions may be read into the working memory 135 from another computer-readable medium, such as one or more of the storage device(s) 125. Merely by way of example, execution of the sequences of instructions contained in the working memory 135 might cause the processor(s) 110 to perform one or more procedures of the methods described herein.

The terms "machine-readable medium" and "computer-readable medium," as used herein, may refer to any article of manufacture or medium that participates in providing data that causes a machine to operate in a specific fashion. In an embodiment implemented using the device 100, various computer-readable media might be involved in providing instructions/code to processor(s) 110 for execution and/or might be used to store and/or carry such instructions/code (e.g., as signals). In many implementations, a computer-readable medium is a physical and/or tangible storage medium and/or memory storage device. Such a medium may take many forms, including, but not limited to, non-volatile media, volatile media, and transmission media. Non-volatile media may include without limitation optical and/or magnetic and/or solid state drives, such as the storage device(s) 125. Volatile media include, without limitation, dynamic memory, such as the working memory 135. "Computer readable medium," "storage medium," and other terms used herein do not refer to transitory propagating signals. Common forms of physical and/or tangible computer-readable media include, for example, a floppy disk, a flexible disk, hard disk, magnetic tape, a solid state memory device, or any other magnetic medium, a CD-ROM, any other optical medium, punchcards, papertape, any other physical medium with patterns of holes, a RAM, a PROM, an EPROM, a FLASH-EPROM, or any other memory chip or cartridge.

Various forms of computer-readable media may be involved in carrying one or more sequences of one or more instructions to the processor(s) 110 for execution. Merely by way of example, the instructions may initially be carried on a magnetic disk and/or a solid state memory device and/or optical disc of a remote computer.

The communications subsystem 130 (and/or components thereof) generally will receive the signals, and the bus 105 then might carry the signals (and/or the data, instructions, etc. carried by the signals) to the working memory 135, from which the processor(s) 110 retrieves and executes the instructions. The instructions received by the working memory 135 may optionally be stored on a non-transitory storage device 125 either before or after execution by the processor(s) 110.

In this embodiment of the invention, processor 110 can be a small microcontroller, and communications subsystem 130 can be a Bluetooth radio transmitter/receiver device with antenna. In this embodiment of the invention, working memory 135 can be a flash-memory integrated circuit.

In this embodiment of the invention, multiple one or more input devices 115 can be: a radar system, that can be comprised of one or more of a transmitter, waveguide, antenna, duplexer, and/or receiver, an air pressure sensor device, a touch sensor device, and an internal accelerometer and/or gyroscope sensor device.

In this embodiment of the invention, power device 160 can be a battery.

In this embodiment of the invention, one or more output devices 120 are: electrical stimulator device, an electrical stimulator with two or more electrodes; signal light, an LED light; and two internal mechanical wave generator devices (one in each end of the device), vibration-producing devices.

In this embodiment of the invention, storage device 125 can be a flash-memory integrated circuit.

In this embodiment of the invention, operating system 140 can be machine code that can be read by processor 110 and can guide the functioning of device 100.

In this embodiment of the invention, application 145 can be code that can be read by processor 110 and can guide additional functioning of device 100.

Aspects of the disclosure use sensors to track bodily activity in the oral cavity across one or more states or activity state. A state may be a current configuration or relative orientation of the various parts (e.g., tongue) in the oral cavity. An activity state may be a series of contiguous (or near contiguous) states that together relay information. In certain embodiments, a 3 dimensional (3D) map or model of the oral cavity and any temporal changes to it may be detected over time to determine the various states and activity states. For example, a reference 3D map may be generated for the oral cavity, wherein the 3D map or model is generated using techniques disclosed with respect to FIGS. 6 and 7. A new 3D model is detected/constructed using input from the sensors (radar, pressure, etc.) and a change in the state (using the change in the 3D model/map) of the oral cavity may be used in determining a condition (e.g., command, state).

A number of different techniques may be used for creating a three dimensional map of the oral cavity without deviating from the scope of the disclosure. In certain embodiments, a state or activity state may be detected without using a 3D map. For example, a series of known states detected over time may in itself may be sufficient to infer a certain pattern resulting in a command or communicative indicator.

A variety of different sensors may be used without deviating from the scope of the disclosure. In certain embodiments, air pressure, such as breath and speech activity may be used in determining the states/activity states inside the oral cavity. In other instances, one or more tiny cameras that fit inside your oral cavity may be used for the same purpose of determining states/activity states. In another implementation, waves may be generated from a device to determine the various states and activity states. For example, ultrasonic waves, infrared rays, radar, radio frequency, or any other type of waves may be used in determining the various states of the oral cavity. For example, reflections or absorptions, change in phase of the waves, change in amplitude of the waves, interference of the wave with its reflected waves or other waves may provide information regarding the various states associated with the oral cavity and/or matter within it.

Aspects, techniques, (non-transitory) computer-readable storage medium, and components disclosed with reference to FIG. 1 above may be employed in FIG. 2-11 below. For example, the one or more processors disclosed in FIG. 1 may execute instructions stored in the storage and/or memory in FIG. 1 to perform techniques disclosed in FIG. 2-11. Similarly, other sensors and inter-connection disclosed in FIG. 1 may be employed in carrying out various aspects disclosed in FIGS. 2-11.

Figure 2:
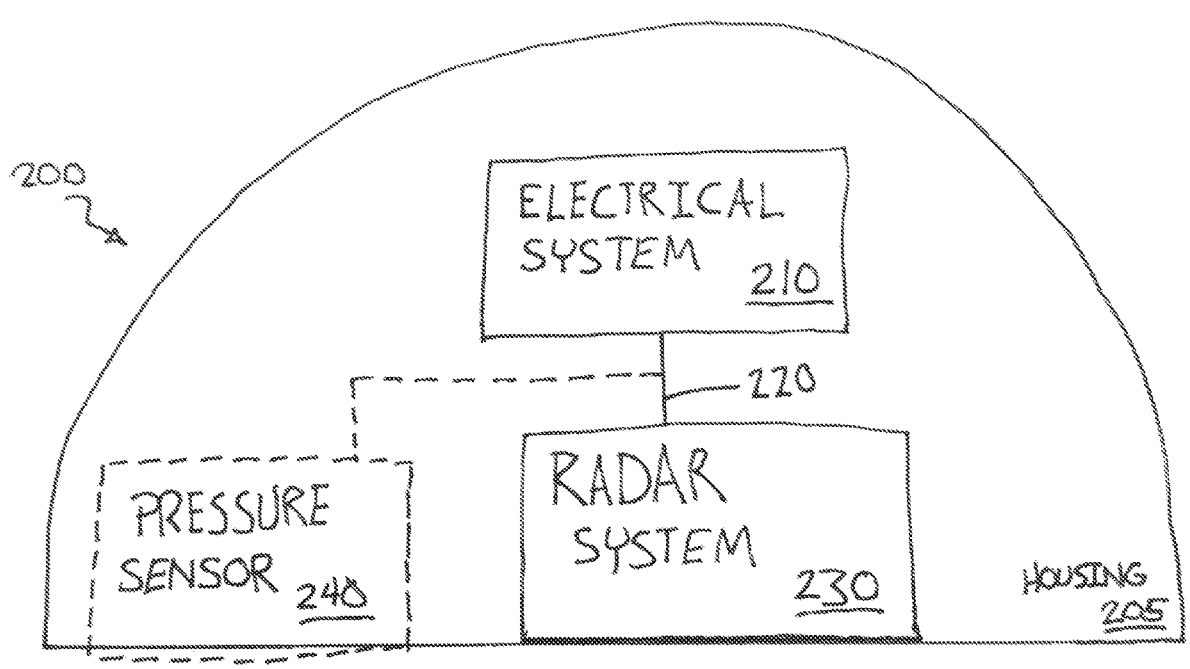
FIG. 2 illustrates an intraoral device according to certain aspects of the disclosure.

FIG. 2 illustrates an intraoral device 200. In some embodiments one or more components of device 200 can be implemented using one or more components and/or techniques disclosed with respect to FIG. 1 or other figures disclosed herein in practicing aspects of the invention. Device 200 is comprised of an electrical system 210 (similar to device 100 of FIG. 1), incorporating into a housing 205 a radar system 230 and/or pressure sensor 240, which can sense air pressure, and linking these into electrical system 210 via a bus 220 as input devices 115. Radar system 230, which can be comprised of one or more of an electromagnetic field (EMF) transmitter, waveguide, antenna, duplexer, and/or EMF receiver, sends out electromagnetic signals and receives electromagnetic reflections from the surrounding mouth environment and/or foreign matter in or around the mouth environment. In certain embodiments, the Radar system 230 may have a transmitter for transmitting the electromagnetic signals and a receiver/sensor for receiving the reflected electromagnetic signals. Depending on the oral cavity, the physical state of the oral cavity, and/or foreign matter in and/or around the oral cavity, radar signals emitted by radar system 230 can bounce off of these structures and/or surfaces and radar system 230 can sense different reflections. The received reflection, sensed by radar system 230, can be processed by one or more processors 110 and/or stored in storage device 125, and/or made available to operating system 140 and/or one or more applications 145.

Received radar reflections from the mouth environment can be processed by processor 110 and/or compared in different ways, such as frequency filtering, frequency shift, time analysis, range Doppler mapping, angle of arrival analysis, micro-Doppler analysis, and/or three dimensional depth mapping.

In frequency filtering, for example, the time between each transmit pulse and/or frequency modulation period of continuous transmission of radar system 230 is divided into range cells, which is also known as range gates. Each cell can be processed, by processor 110 and/or other processing resources, and filtered independently, much like the process used by a spectrum analyzer to produce the display showing different frequencies. Reflections from different objects and/or different distances can produce different spectrums. When produced regularly, these spectra can form patterns that can be associated with the state of, or changes in the oral cavity.

In other embodiments, other input devices 115 can provide other types of data about the mouth environment that can also be processed by processor 110, for instance an air pressure sensor can provide information on air pressure (or simply pressure) in the mouth environment that can be used to track air pressure changes in the mouth environment across time. Information derived from different input devices 115 can be combined into hybrid types of information about the state of the mouth environment and/or user intention. Embodiments disclosed with reference to FIG. 6 and FIG. 7 (that disclose additional details related to techniques associated with air pressure sensors and air pressure) may combined with aspects of the disclosure related to FIG. 2 to provide a more enriched data set for determining conditions associated with the oral cavity.

In frequency shift, in another example, processor 110 can determine radial velocity of the surrounding environment and/or features in the surrounding environment by analyzing how motion in the environment has altered the frequency in the reflection of the transmissions of radar system 230, a faster-than-transmitted frequency indicating decreasing distance from device 200, and a slower-than-transmitted frequency indicating increasing distance from device 200.

In time analysis, processor 110 can determine distance to the surrounding environment and/or features in the surrounding environment by analyzing the time between transmissions of radar system 230 and the reflections of that signal received by radar system 230, and/or calibration data from other sensors. Shorter interims indicate shorter distances, and longer interims indicate longer distances.

In Range Doppler mapping, processor 110 can combine frequency filtering, frequency shift, and time analysis methods to provide both a radial velocity and range of the surrounding environment and/or features in the surrounding environment.

In angle of arrival analysis, processor 110 can determine the direction of signal measured by radar system 230 by analyzing the difference measured in received phase at each element in the antenna array of radar system 230. The delay of arrival at each element is measured directly and converted to an AoA measurement.

For example, a wave, incident boresight upon a two element antenna array spaced apart by one-half the wavelength of an incoming RF wave, will arrive at each antenna array simultaneously. This will yield 0° phase-difference measured between the two antenna array elements, equivalent to a 0° AoA. If a wave is incident upon the array at broadside, then a 180° phase difference will be measured between the elements, corresponding to a 90° AoA.

In three dimensional depth mapping, processor 110 can build a three dimensional map of the mouth environment by combining data created with range Doppler mapping and angle of arrival analysis.

In micro-Doppler analysis, processor 110 can analyze sideband frequency modulations in the radar reflection of the oral environment returned to radar system 230, which are called the micro-Doppler effect. Specific types of matter can be associated with specific types of micro-Doppler signatures, and processor 110 can use micro-Doppler signatures to differentiate and identify specific types of matter, such as tissues in the mouth environment, and/or different types of liquids or solids, such as tongue tissue, enamel, and/or milk.

Air pressure sensor 240 can be used to measure air pressure and air pressure change over time in the oral environment, which can be processed by processor 110 and/or stored in storage device 125. Air pressure information can be measured regularly and can be graphed to show a pattern of breathing, vocalisation and/or sub-vocalisation as air pressure in the oral environment is influenced by the respiratory system's functions, such as expansion and contraction of the lungs and/or diaphragm, and/or the voice system's functions, such as producing human speech.

Figure 3:
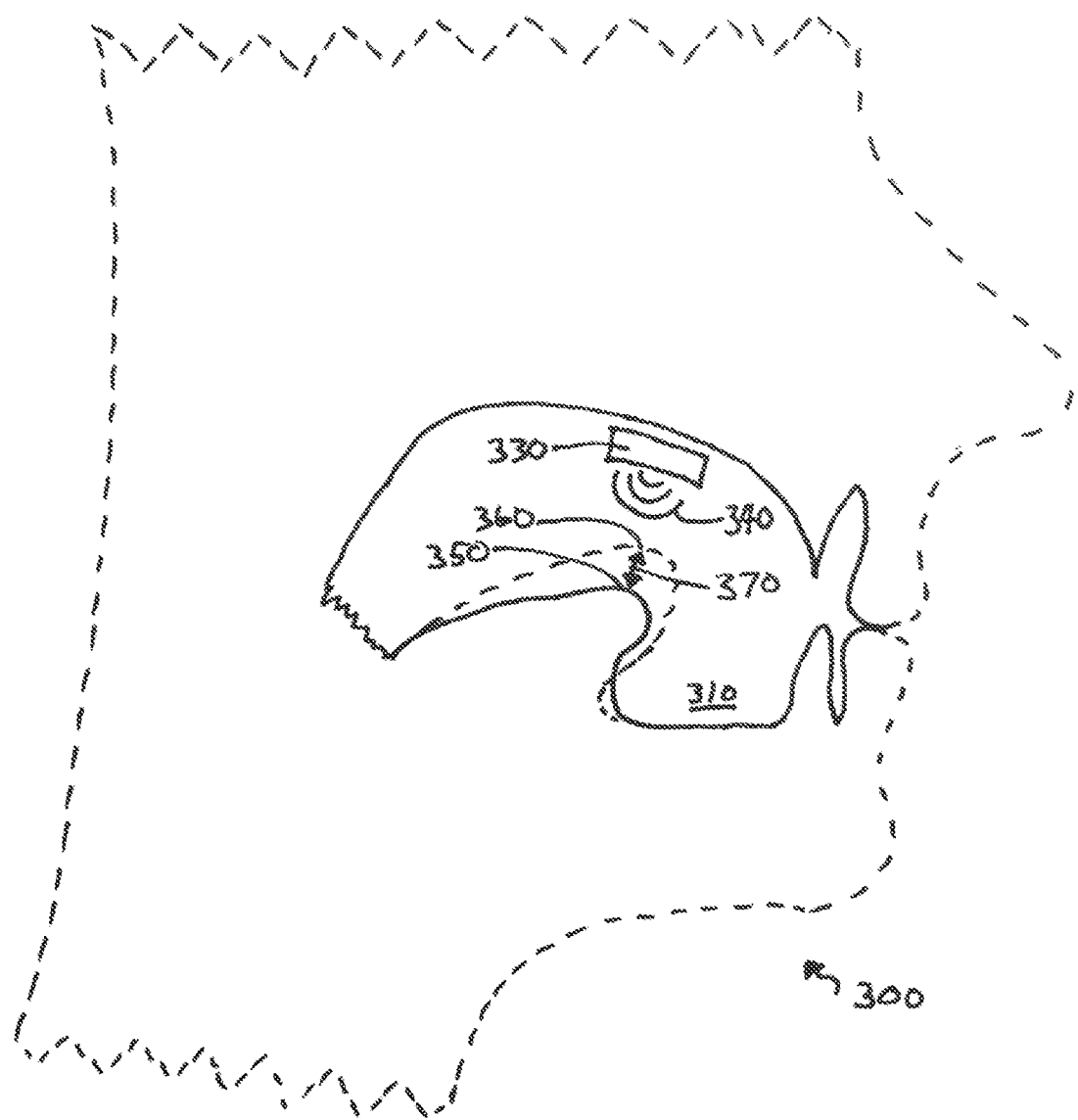
FIG. 3 illustrates, in cross-section, usage, of an example device, situated in an oral cavity, according to certain embodiments of the disclosure.

FIG. 3 illustrates, in cross-section, usage 300, of an example device 330, situated in an oral cavity 310, sensing via a radar transmissions 340 a change 370 in oral cavity 310 of a feature position 350 from a feature position 360. In some embodiments, one or more components of device 330 can be implemented using one or more components and/or techniques disclosed with respect to FIG. 1, FIG. 2, and/or other figures disclosed herein in practicing aspects of the invention. Radar transmissions 340, which can occur constantly and/or at intervals, will be reflected back to device 330 differently from oral cavity 310 as changes, like change 370, occur. Input devices 115, such as radar system 230 and/or pressure sensor 240, processor 110, applications 145, and other components of embodiments of the invention can be configured to track different features and/or changes in mouth environments like oral cavity 310, such as angle of arrival for different features, three-dimensional positioning of features, orientation of features, velocity of features, and/or radial velocity of features. These measurements can be used to create data structures that describe the oral cavity 310, comprising a multi-dimensional map of structures in and/or of the mouth environment, and/or a stream of information and/or events related to the nature and/or changes to structures and/or features in and/or around the mouth environment.

Changes in mouth environment 310, such as change 370, can occur in the physical state of the mouth environment, such as a person moving her tongue, slightly opening her jaw, and/or taking a breath, and features and/or information corresponding to features can be tracked and stored in storage devices like storage device 125. In other embodiments, different sensors might provide data about change of different natures, such as an accelerometer sensor providing data about movement and/or vibration data of a mouth environment.

Change 370 can illustrate a particular condition that can be associated/interpreted as a command and enacted by processor 110. Based on the tracking of features, conditions can be determined, for instance, if a feature crosses some threshold, like a person moving her tongue more than a threshold distance toward the device, and processor 110 making a determination to use its communication subsystem 130 to communicate with an external service, turning on a light next to the user. Information about a condition can be stored in storage device 115, and used by processor 110, operating system 140 and/or applications 145 and/or other components and/or modules of the device. Conditions of the oral cavity environment might be associated with many aspects of the user's state.

Figure 4:
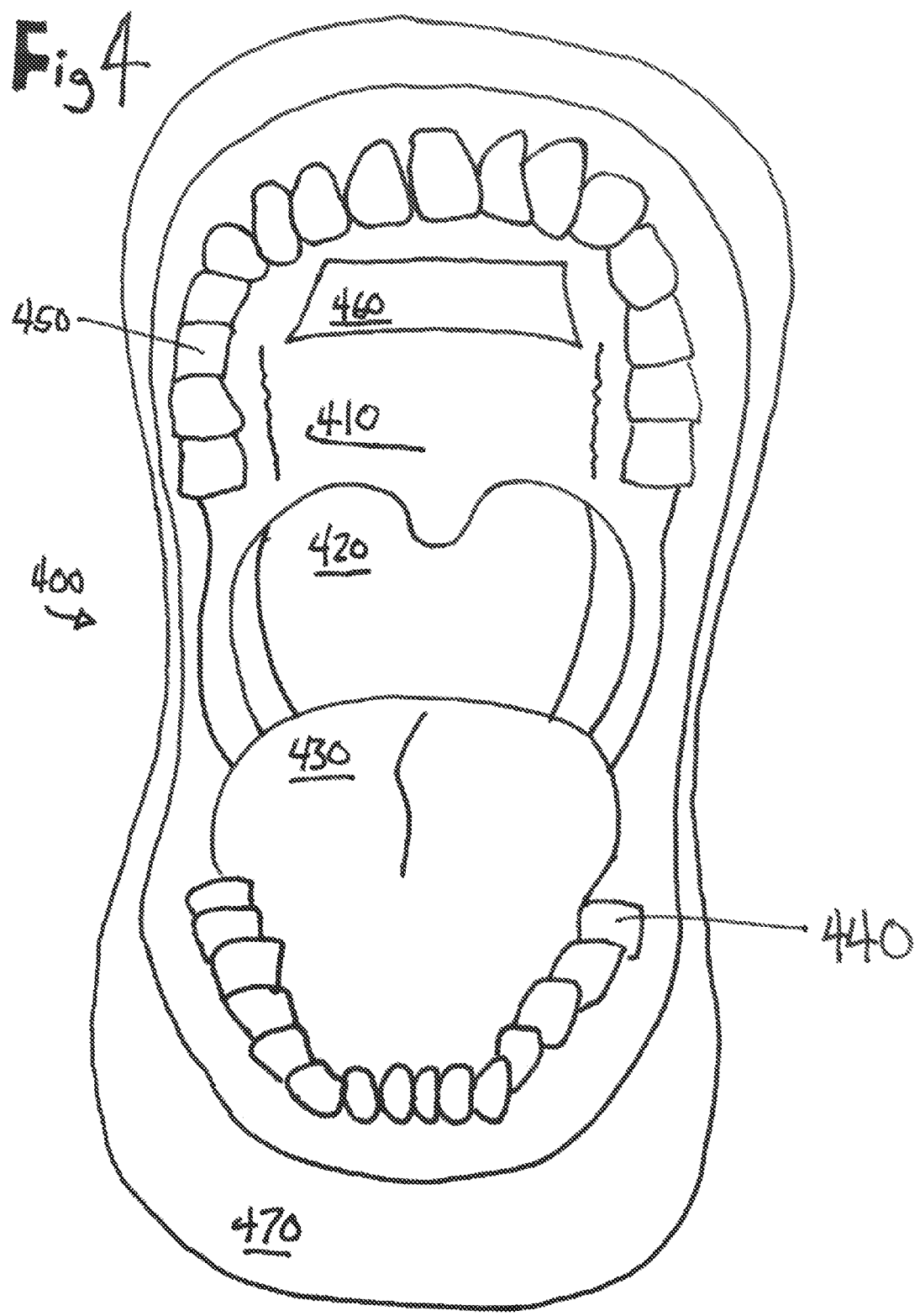
FIG. 4 illustrates an example device in an example placement and purview of an oral cavity environment, according to certain embodiments of the disclosure.

FIG. 4 illustrates an example device 460 in an example placement and purview of an oral cavity environment 400, comprised of a maxilla 450, a mandible 440, a palate 410, a fauces and pharynx 420, lips 470, and a tongue 430. In some embodiments, one or more components of device 460 can be implemented using one or more components and/or techniques disclosed with respect to FIG. 1, FIG. 2, FIG. 3, and/or other figures disclosed herein in practicing aspects of the invention. The vantage point of device 460 allows it to observe the state of oral cavity environment 400 and, using sensors like radar system 230 and/or air pressure sensor 240, to take readings and capture information about the state of oral cavity environment 400 that can be stored, for instance in storage devices like storage device 125, and/or processed, for instance by processor(s) 110, into data structures like a 3d map of oral cavity environment 400, and/or a stream of information and/or events related to the nature and/or changes to structures and/or features in and/or around the mouth environment.

Device 460's placement within oral cavity environment 400, nestled in the maxilla, allows device 460 to maintain a position in relationship to the rest of the head, which allows readings of radar system 230 to track distances and motion of the mandible 440, which can be used as a signal about jaw movement. Other placements of device 460 are possible, with differing benefits and/or opportunities for observation. Placement on the outside or around the maxilla and/or mandible avoids taking up space in the center of oral cavity 460 and allows more direct observation of the cheeks, lips, face, and external world, and/or proximity to external charging systems. Placement inside the mandible 440 allows mandible 440 to act as the frame of reference against which movement is measured. This has advantages, such as more careful observation of the tongue, which can move with mandible 440.

Because of device 460s placement in oral cavity environment 400, sensors such as radar system 230 and/or pressure sensor 240 allow device 460 to observe features like intraoral pressure and/or a portion of the tongue, and/or shape and/or geometric characteristics of the tongue and/or portions of the tongue, and how they change over time. For instance, intraoral changes during vocalizations, such as speech, and/or speech-like sub-vocalizations and/or intraoral posture can be observed by device 460 as users form certain sounds and/or words and/or mouth shapes and those changes can be associated with conditions related and/or unrelated to those words or sounds. For instance, observing the intraoral cavity while a user says "Play Music" might match a condition for a user's mouth moving in that shape and cause processor 110 to issue commands via its communications subsystem 130 to an external device, instructing it to play music for the user. For example, changes in the pressure model of the oral cavity, 3D model of the oral cavity or tracking of various parts of the oral cavity can provide enough information for the system (i.e. device) disclosed herein to infer a particular condition/command associated with the change in the oral cavity environment with or without the associated vocal (i.e. sound) information.

Figure 5:
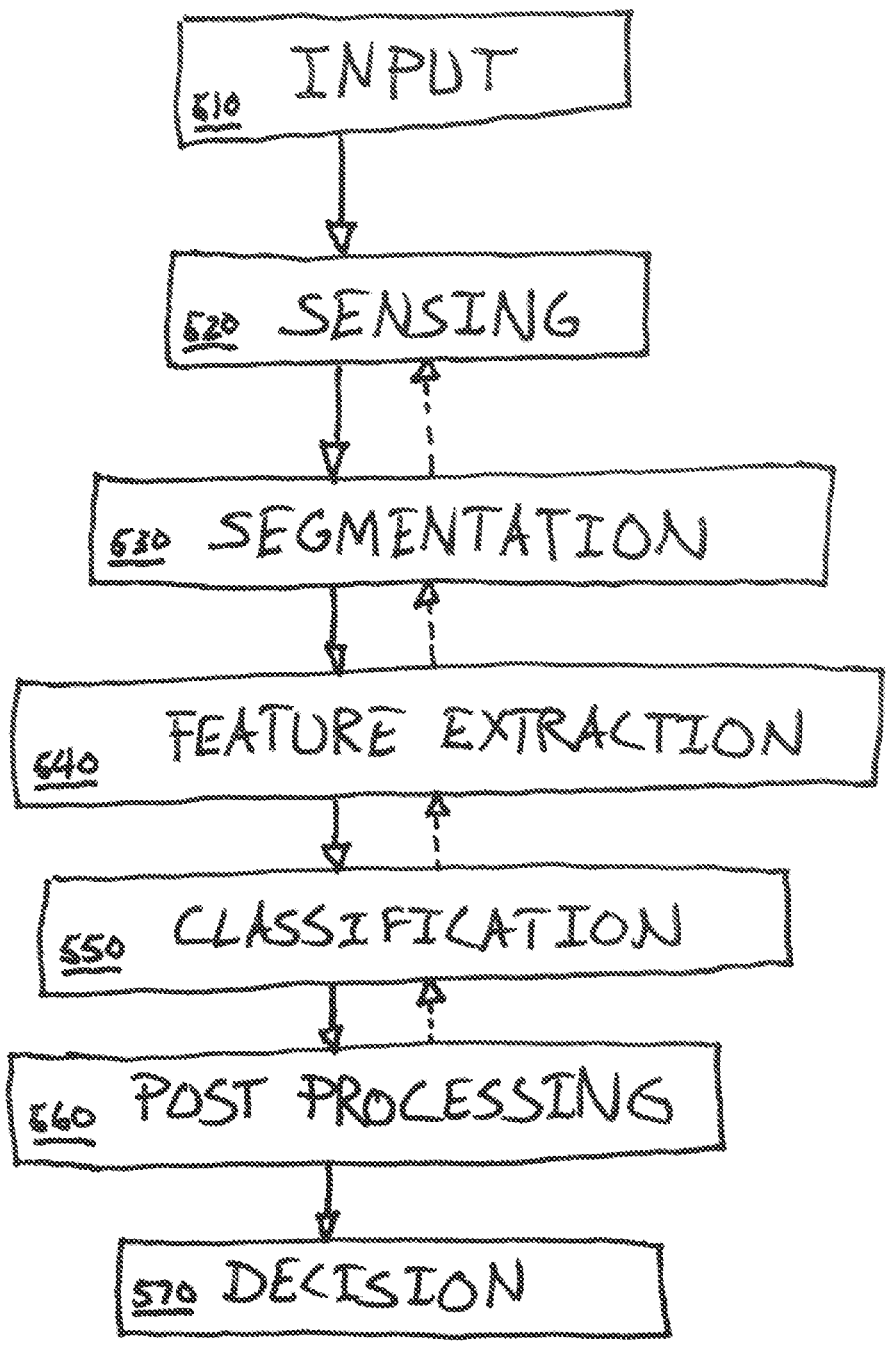
FIG. 5 is a block diagram illustrating a process of making a decision, based on an input that can, in certain embodiments, can be from an oral cavity and/or oral cavity environment.

FIG. 5 is a block diagram illustrating a process 500 of making a decision 570, based on an input 510 that can be from an oral cavity 310 and/or oral cavity environment 400. In some embodiments, one or more steps of process 500 can be implemented using one or more components and/or techniques disclosed with respect to FIG. 1, FIG. 2, FIG. 3, FIG. 4, and/or other figures disclosed herein in practicing aspects of the invention. Furthermore, several steps disclosed with respect to FIG. 5 may operate or may be further augmented by steps, techniques, methods or processes disclosed with respect to FIG. 8. Process 500 includes a sensing 520 of input 510, which could be a data produced by radar system 230 about reflections of radar transmissions 340, a segmentation 530 of that data, a feature extraction 540 from that data, a classification 550 using that data, a post-processing 560 of that data, and then making a decision 570 based on that data. This process allows a situation where an intraoral device, such as device 460, can make determinations about the state of and changes to the state of an oral cavity environment 400 such as determining if a portion of the tongue is near or far from device 460.

Segmentation 530 for input to radar system 230 might be accomplished by frequency filtering, frequency shift, time analysis, range Doppler mapping, angle of arrival analysis, micro-Doppler analysis, dimensional depth mapping, and/or other methods, for instance by using frequency filtering to segment reflections of oral cavity environment 400 sensed by radar system 230 into range cells, or by using micro-Doppler analysis to distinguish and segment data sensed about reflections of oral cavity environment 400. Other inputs can be segmented by these and/or other, similar methods as suitable to each sensor's type of data.

Feature extraction 540 can take segments and characterize a feature to be recognized by measurements whose values are very similar for features in the same category. For instance, input to radar system 230 from tissue at the edges of tongue 430 might exhibit a certain characteristic relating to radar reflectivity within a certain range cell that processor 110 can use to associate it as having that pattern in a feature extraction 540. Repeating this process for different useful characteristics builds up many features associated with portions of segments.

Features can be comprised of: portions, edges, shapes, curves, EMF reflectivity, distance, positioning, velocity, micro-Doppler rotation and/or vibration, tissue type, material type among others. In certain embodiments, pressure and change in pressure may also be associated with certain features and may be used as part of the feature extraction 540 process.

Classification 550 looks for a feature vector (an n-dimensional vector of numerical features that represent something) associated with a classification. For instance processor 110 might use tongue edge, micro-Doppler tongue signatures, and/or teeth edge to classify an area in a three-dimensional map of oral cavity environment 400 as the tongue. Additionally, the tongue area could be broken down into portions of the tongue, with a marker feature identifying the center of the tip of the tongue, for instance.

Post-processing 560 uses the output of classification 550 to decide on actions, for instance updating a three-dimensional map of the mouth after classifying an area of tongue that was previously not the tongue.

Finally, decision 570, is the result stemming from post-processing 560 which, for instance, can be carried out by processor 110, updating the three-dimensional map of oral cavity environment 400.

Outputs of parts of the process can be used as feedback in other parts, depicted in FIG. 5 by dotted-line arrows going. This feedback can be used to tune parts of the system. For instance, classification 550 might classify an object as part of a tongue 430, and this information can be sent back to other parts of process 500 as an input to further adjust the process, for instance to segmentation 530, and there used to change the way segmentation carries out range cell partitioning in order to better partition signals related to tongue tissue.

Figure 6:
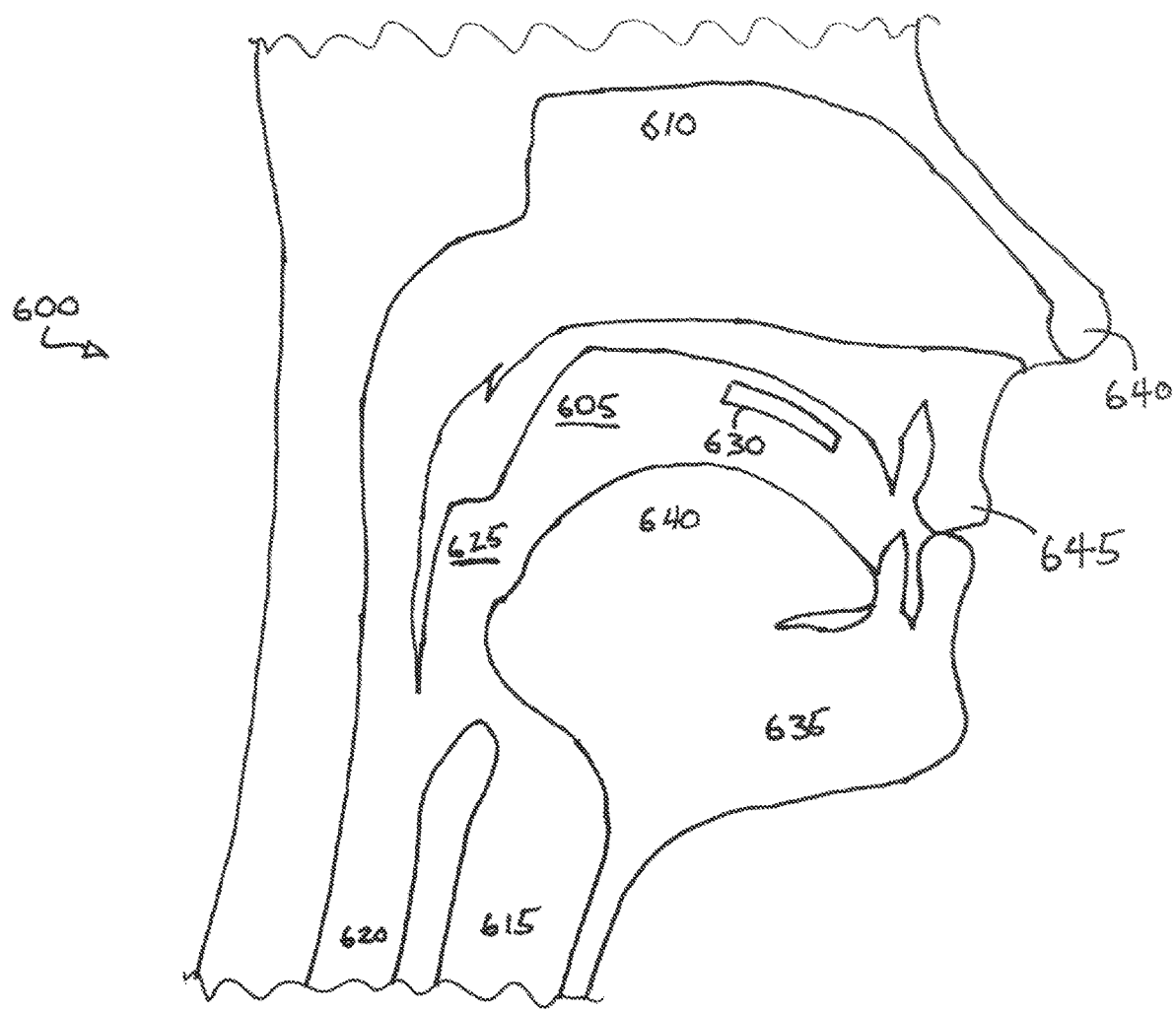
FIG. 6 illustrates an example purview of a device in a cross-section profile of a human head and neck, with a cutaway of an oral cavity environment and connected airways

FIG. 6 illustrates an example purview 600 of device 630 in a cross-section profile of a human head and neck, with a cutaway of an oral cavity environment 605 and connected airways, which can be comprised of nasal cavity 610, fauces 625, trachea 615 (which leads to the lungs), nose 604, lips 645, and/or esophagus 620. Mandible 635 supports tongue 640 under device 630. In some embodiments, one or more components of device 630 can be implemented using one or more components and/or techniques disclosed with respect to FIG. 1, FIG. 2, FIG. 3, FIG. 4, FIG. 5, and/or other figures disclosed herein in practicing aspects of the invention. Because air pressure within these systems is linked, device 630 can monitor the respiration of the user through either nose 604, and/or lips 645 from the oral cavity environment 605 using inputs like air pressure sensor 240, which monitors the air pressure of oral cavity environment 605. Other sensors can be used to capture additional input about the state of oral cavity environment 605 and its relationship to respiration, such as a three-dimensional accelerometer system, which measures force and acceleration in three-dimensional space and can measure orientation to compass direction and can be used to map vibrational changes that occur during the respiration process over time, and/or a gas sensor or sensors which can measure characteristics about the makeup of the gas in the oral cavity environment and can be used to map changes to gas type or composition over time, and/or other sensors and/or inputs.

FIG. 7 is a graph of multiple respiration aspects over time 700. Device 630 can analyze intraoral air pressure 725 over time 703, input that can be sensed and graphed as intraoral pressure change 733. In some embodiments, one or more aspects of FIG. 7 can rely on using one or more components and/or techniques disclosed with respect to FIG. 1, FIG. 2, FIG. 3, FIG. 4, FIG. 5, FIG. 6, and/or other figures disclosed herein in practicing aspects of the invention. Further, the process of FIG. 5 can be applied to this data, segmenting, feature extracting, and classifying sensed input on intraoral pressure change 733 into more data, such as single respiration cycles with a respiration cycle start 705, a respiration cycle middle 713, a respiration cycle end 710, an inspiration phase 715, and/or an expiration phase 718. Other sensor data and/or data, if present, can also be used in this process to create more data about the user's state and changes. For instance, with intraoral pressure change 733, because we know the general shape of corresponding parts of the respiration cycle, we can make estimations for airflow 723 and lung volume 720 values corresponding to intraoral air pressure 725 values, which can be graphed along with intraoral pressure change 733 as in FIG. 7, as airflow change 730 and lung volume change 728.

Some embodiments can use respiration models as described in respect to FIG. 6 and FIG. 7 and/or other data and/or sensors to identify the user's mental state, intentions, commands, and other conditions. For instance, the device might detect an irregular breathing pattern that is associated with increased levels of stress. Respiration data can be used to build detailed models of the user's respiration as in FIG. 7, and/or be used as an input to other models, and/or be used as an input to make decisions, as in FIG. 5. Respiration information and events can be used to provide feedback to the user, such as biofeedback, in order to reinforce and/or change breathing behavior, and/or to determine actions of the device. For instance, to instruct the device to switch modes, a user might blow three quick puffs of breath out through the mouth or nose. Arriving at a decision that this condition, pre-associated with the mode change, has occurred, processor 110 could enact the mode change.

FIG. 8 is a block diagram is an example of one machine learning process, supervised classification, that can be implemented in some embodiments of the invention to classify and label information derived and/or partially derived from input from an oral cavity environment 400, and other machine learning processes might be used in other embodiments. In training step 810, machine learning algorithm 860 is fed correctly-labelled training corpora for each input, pairs of labels and feature sets about intraoral data the embodiment wants to classify, which sets feature extraction 840 and features 850, and allows machine learning algorithm 860 to create a machine learning model.

During prediction step 820, feature extraction step 880 is used to process unlabelled input, for instance, data sensed from oral cavity environment 400, into sets of features 885, which is then processed in classifier model step 890 to associate relevant labels. This process can be used, for instance, to build a 3D model of the state of the mouth from input devices 115 like radar system 230, and/or to identify tongue 440 and/or track a change 370 to it.

Because oral environment 400 has a purview into myriad bodily functions, for instance: respiration, digestion, vocalization, etc., and is comprised of multiple expressive tissues, for instance: the tongue, cheeks, lips, and because input devices like radar system 230 and/or pressure sensor 240 can sense oral environment 400 and changes to oral environment 400 by sensors in an embodiment of the invention like device 460 and/or 630 and interpret multiple degrees of freedom that can be tracked and or observed in oral environment 400 and/or updated into a 3D model of oral environment 400.

Output from some steps may be used as inputs in others, for instance by correcting errors in classification by classification model 890 and using this as an input 830 to help fine tune machine learning algorithm 860 in creating a more accurate model. Models can be created using data about a single person's oral environment 400, or multiple people's, later described as crowdsourcing. One advantage of this is the ability to find and more-accurately look for certain conditions in oral environment 400 that are similar across multiple people. One embodiment might use this advantage by creating and storing fine-tuned conditions in a storage device 125 that can be used to very accurately identify respiration cycles and events as seen in FIG. 7. One embodiment might use this advantage by creating conditions that accurately predict mental states such as anger, hunger, melancholy, etc, by feeding previous observations about these states as labelled sensor data into training step 810, use these conditions to log this data, and/or issue commands based on these conditions, delivering biofeedback to the oral environment 400, for instance, and/or to issue some related command, such as causing processor 110 to take action to order food to be delivered to the user.

In some embodiments, one or more steps the process described in FIG. 8 can be implemented using one or more components and/or techniques disclosed with respect to FIG. 1, FIG. 2, FIG. 3, FIG. 4. FIG. 5, FIG. 6, FIG. 7, and/or other figures disclosed herein in practicing aspects of the invention.

FIG. 9 is a flow diagram of an example embodiment for determining a condition using pressure. In some embodiments, one or more steps the process described in FIG. 9 can be implemented using one or more components and/or techniques disclosed with respect to FIG. 1, FIG. 2, FIG. 3, FIG. 4, FIG. 5, FIG. 6, FIG. 7, FIG. 8, and/or other figures disclosed herein in practicing aspects of the invention. For example, certain aspects of FIG. 9 may be implemented using instructions executed on a processor 110 that are stored in memory and/or a non-transitory computer-readable storage medium.

At step 902, the device placed in an oral cavity detects air pressure (or simply pressure) in the oral cavity. In another embodiment, the device may detect pressure repeatedly over time or detect the change in pressure over time. The air pressure may be measured using one or more air pressure sensors disposed in the device or elsewhere in the oral cavity (but communicatively coupled to the device).

At step 904, the same or another device may determine a condition based on the pressure detected in the oral cavity. As disclosed in FIG. 6 and FIG. 7 in greater detail, various air passages connecting the oral cavity, the nasal passage and also the ears are interconnected. Pressure change in one cavity can change the pressure associated with another cavity. Especially, breathing or respiration by a user can change the pressure associated with one or more cavities. The device may locally (or at a remote server) develop a pressure model for the oral cavity and detect various states using changes in the pressure model, determine and associate various states with conditions. In one embodiment, the determination of the condition may also be performed using information not only from one device placed in one oral cavity for a user, but by several devices place in several oral cavities and associated with several users (as disclosed in FIG. 11). Examples of conditions may include emotional, mental or physical state of the user. For example, certain changes in the breathing patterns may indicate changes in mood, stress reactions, seizures, or even death.

At step 906, optionally, the device provides feedback in the oral cavity. In one embodiment, the feedback is physical change in the pressure and/or a vibration and/or vibrations. Feedback may include biofeedback, in order to reinforce and/or change breathing behavior, and/or to determine actions of the device.

FIG. 10 is a flow diagram of an example embodiment for determining a condition based on tracking a feature in the oral cavity.

In some embodiments, one or more steps the process described in FIG. 10 can be implemented using one or more components and/or techniques disclosed with respect to FIG. 1, FIG. 2, FIG. 3, FIG. 4, FIG. 5, FIG. 6, FIG. 7, FIG. 8, FIG. 9, and/or other figures disclosed herein in practicing aspects of the invention. For example, certain aspects of FIG. 10 may be implemented using instructions executed on a processor 110 that are stored in memory and/or a non-transitory computer-readable storage medium.

At step 1005, the device placed in an oral cavity identifies a feature in the oral cavity. In some embodiments, the physical state and/or change may be measured using one or more radar systems, disposed in the device or elsewhere in the oral cavity (but communicatively coupled to the device). As described in other figures, At step 1010, the same device may track a feature in or of the oral cavity repeatedly over time and/or detect a change in the physical state of the oral cavity over time.

At step 1015, the same or another device may determine a condition based on tracking the state of the oral cavity environment and/or the state of a 3D model of the oral cavity environment. Communication with other devices can be accomplished via one or more communications subsystems 130, as described in FIG. 1 and FIG. 5 and FIG. 8 describe making decisions that can be based on an input 510 from a mouth environment. The device may locally (or at a remote server) develop a tracking and/or 3D model for the oral cavity and detect various states using changes in the model, determine and associate various states with conditions. In one embodiment, the determination of the condition may also be performed using information not only from one device placed in one oral cavity for a user, but by several devices place in several oral cavities and associated with several users (as disclosed in FIG. 11). Examples of conditions may include states that characterize or stem from emotional, mental or physical state of the user. For example, certain changes in tongue activity patterns may indicate changes in mood, stress reactions, vocalizations, commands, etc. Other examples of conditions might be the manipulations or signature of the oral cavity involved in speaking a word. Conditions can be associated with commands or portions of commands. For instance, a user might speak the words "Turn on lights," and the associated oral manipulations are interpreted as a command to processor 110 to instruct an external system, via communications subsystem 130 to activate the lights in the user's house.

At step 1020, optionally, the device provides feedback in the oral cavity. In one embodiment, the feedback is a physical change in the pressure and/or a vibration and/or vibrations. Feedback may include biofeedback, in order to reinforce and/or change breathing behavior, and/or to determine actions of the device.

In certain other embodiments, one or more tiny cameras that fit inside your oral cavity may be used for the same purpose of determining states/activity states. In another implementation, waves may be generated from a device to determine the various states and activity states. For example, ultrasonic waves, infrared rays, radar, radio frequency, or any other type of waves may be used in determining the various states of the oral cavity. For example, reflections or absorptions, change in phase of the waves, change in amplitude of the waves, interference of the wave with its reflected waves or other waves, or any methods previously mentioned of wave analysis may provide information regarding the various states associated with the oral cavity and/or matter within it. In some embodiments, machine learning, crowdsourcing, and or data analysis methods are employed to identify features within the oral cavity.

FIG. 11, above, is an example system figure for a simplified crowdsourcing system, wherein the server 1102 receives data from a plurality of devices (1108a, 1108b, 1108c, and 1108d). In some embodiments, one or more components described in FIG. 11 can be implemented using one or more components and/or techniques disclosed with respect to FIG. 1, FIG. 2, FIG. 3, FIG. 4, FIG. 5, FIG. 6, FIG. 7, FIG. 8, FIG. 9, FIG. 10, and/or other figures disclosed herein in practicing aspects of the invention. The server may be configured to wirelessly or through a wired connection receive information from the plurality of devices. The server 1102 may comprise several components similar to the components described with reference to FIG. 1, for receiving information, processing information, storing information, communicating information and performing several other functions for carrying out embodiments of the disclosure described herein.

As shown in the above figure, several users (1106a, 1106b, 1106c and 1106d) may use a device (1108a, 1108b, 1108c, and 1108d, respectively) disposable in the oral cavity, wherein the self-contained device comprises a first memory. The first memory may be a volatile or non-volatile memory for temporarily storing information detected by the device.

These users may be referred to as test subjects elsewhere in the disclosure. The devices may wirelessly or through a wired connection send information to the server 1102. In some instances, the devices may send information through intermediary access points (1110a, 1110b) and/or a series of computer systems and routers placed in a network 1104 to the server 1102. In some embodiments the server 1102 is not a dedicated server, but resources associated with a server allocated from a plurality of servers placed inside a cloud service.

In some instances, the server 1102 may be operated by a research center for drawing inferences from data received from a plurality of devices. In certain implementations, the plurality of devices 1108a, 1108b, 1108c and 1108d and/or the server 1102 may be configured to anonymize the data before transmitting and storing the data for further processing. For example, anonymizing the data may comprise removing any information associated with the data that may uniquely identify any user from the plurality of users. For example, anonymizing the data may comprise, removing the user name, birth month and day, device identifier (e.g., IP address, MAC address), location, etc.

In some instances, the server 1102 may further process the data received from the plurality of devices to draw inferences between certain 3D models of the oral cavities, conditions associated with the oral cavities, pressure models associated with the various oral cavities, and/or characteristics detected from the oral cavity and certain conditions for the user. For example, in one simplified example, a device may detect particular patterns at a particular time or period of time. In addition, during the same period of time the user may provide information regarding a certain condition associated with the user. For example, the user may indicate that the user is very angry. Additional information regarding the user, such as age, height, and/or body weight may be used in coloring the information received from the user device. The data associated with the various users can be used as enriched datasets for the machine learning aspects disclosed with respect to FIG. 8 to determine various conditions associated with the user that may include emotional, mental and physical states of the user, or it may include learning various commands and languages common between multiple sets of users.

The server 1102 may collect several samples of data comprising similar information from the same device and several other devices. In some instances, the server 1102 may receive thousands of data points. For example, components of the server 1102 may be configured to draw inferences and correlations between the detected speech patterns with associated movements of the tongue and/or pressure and other oral cavity characteristics and patterns using the several samples of data received from several devices over a period of time. Furthermore, as more devices provide more associations over time, the server 1102 can continually improve the associations between patterns.

Once the server 1102 has enough information to draw acceptable inferences, the server 1102 may update the devices with indicators that alert the user of the condition or the onset of the condition. For example, the device upon detection of the patterns that have been observed in the past before the onset of a particular condition by providing the user with an indication (e.g., vibration).

It should be noted, that speech is provided as an example and many other patterns may be detected and controlled. In some instances, the device used for a user may also be programmed and personalized for a user, based on previous data associated with the user. In such instances, the data may not be anonymized, but stored separately. In certain instances, the data may be stored with additional encryption and privacy disclosures to the user.

In some embodiments, aspects of the disclosure may detect speech using a number of techniques such as using the tongue position and air pressure ("ay" sound versus "oh" sound). In certain other embodiments, the breathing pattern and/or air pressure may reveal the state of a person, such as if the person is speaking or not speaking.

In certain embodiments, the state and/or activity of the tongue in the oral cavity may be tracked to determine certain commands or conditions. For example, the change in the shape of the tongue and/or movement associated with the tongue may indicate a command or condition. For example, the shape of the tongue may change to fat, flat, small, thick, pointed, etc. The tongue can be moved from side to side, up and down, back and forth and be used to touch and manipulate controls placed inside the oral cavity and/or and/or control areas to indicate certain commands. For instance, a user might touch the tongue to a certain tooth in order to cause processor 110 to issue a command. This type of condition has the added benefit of creating a physical form of biofeedback to the action.

Once sensor data is created and/or certain features are identified, machine learning techniques may be used for feature extraction to identify states. Certain states or activity states may be used in determining language, action, and/or commands. For example, the tongue may be used in conjunction with other parts of your oral cavity in making "W" sound, across all the test subjects, Whenever, you make a "Kay" shape with your mouth, the device sees and interprets that as the user inputting or typing a letter W.

In some embodiments, the motion and/or motions of the tongue or tongue tip in the mouth may be mapped to motion of other objects outside the oral cavity. For example, in certain instances, the movement of the tip of the tongue in one direction may be mapped to the motion of a prosthetic limb, allowing the motion of the tongue to control the motion of the prosthetic limb. The movement of the tongue in the 3D model of the oral cavity may be converted to commands and sent using a wired and/or wireless communication means to an external device that is coupled to a mechanical device capable of moving objects in a direction indicated based on commands from a device located inside the oral cavity.

In certain other embodiments, the motion of the tongue may be used as a cursor or control virtual or augmented reality. In other embodiments, a device placed in the oral cavity may provide feedback from the augmented and/or virtual reality to the user. For example, the vibrational or engraved deformations of the surface of the device may provide haptic feedback to the user, creating/and/or enhancing their virtual/augmented reality experience.

In certain embodiments, speech identification may be used to determine the mode of interaction with the user. For example, the device may postpone interaction until the person is done talking or the device may enhance its interaction with the user while the person is talking to grab the user's attention.

Some embodiments track respiration, which might take place through the nose, by sampling gas pressure from inside the oral cavity. The two cavities are connected and will feel similar pressure. Likewise, a sound sensor or sensors, and/or other sensors in the mouth could also track nasal, stomach, vocal-chord, and/or other bodily processes and/or sounds, as well.

What is claimed:

1. A method, comprising:
   identifying, using a radar system in a device placed in an oral cavity, a feature in the oral cavity;
   tracking, using the radar system in the device placed in the oral cavity, the feature in the oral cavity; and
   determining, using a processor in the device placed in the oral cavity, a condition based on the tracking of the feature in the oral cavity, wherein the condition represents a mental state of a person and the mental state is associated with the condition by processing the feature through a classifier model to determine the condition.

2. The method of claim 1, wherein the feature is one or more of a portion of a tongue, a deformation in the tongue, a marker on the tongue, or a geometric characteristic of the tongue.

3. The method of claim 1, wherein the tracking the feature is performed by transmitting two electromagnetic signals and receiving the reflection of the two transmitted electromagnetic signals from the feature at the device and determining a change in a position of the feature, based on the change in the reflections of the transmitted electromagnetic signals.

4. The method of claim 1, wherein the tracking the feature is performed by sampling reflected electromagnetics signals at the device and determining a change in the sampled reflected electromagnetic signals.

5. The method of claim 1, wherein information associated with the condition is stored at the device.

6. The method of claim 1, further comprising the device communicating wirelessly with an external device to perform a function based on determining of the condition.

7. The method of claim 1, wherein the device provides physical stimulus as feedback to a tissue in the oral cavity.

8. A device placed in an oral cavity, comprising:
   a radar, placed in the oral cavity, for transmitting and receiving electromagnetic signals in the oral cavity;
   a processor, placed in the oral cavity, configured to:
      identify a feature using the received electromagnetic signals a feature in the oral cavity;
      track the feature in the oral cavity; and
      determine a condition based on the tracking of the feature in the oral cavity, wherein the condition represents a mental state of a person and the mental state is associated with the condition by processing the feature through a classifier model to determine the condition.

9. The device of claim 8, wherein the feature is one or more of a portion of a tongue, a deformation in the tongue, a marker on the tongue, or a geometric characteristic of the tongue.

10. The device of claim 8, wherein the tracking the feature is performed by transmitting two electromagnetic signals and receiving the reflection of the two transmitted electromagnetic signals from the feature at the device and determining a change in a position of the feature, based on the change in the reflections of the transmitted electromagnetic signals.

11. The device of claim 8, wherein the tracking the feature is performed by sampling reflected electromagnetics signals at the device and determining a change in the sampled reflected electromagnetic signals.

12. The device of claim 8, further comprising the device communicating with an external device wirelessly to perform a function based on determining of the condition.

13. The device of claim 8, wherein the device provides physical stimulus as feedback to a tissue in the oral cavity.

* * * * *